(12) United States Patent
Take et al.

(10) Patent No.: US 11,141,504 B2
(45) Date of Patent: Oct. 12, 2021

(54) FRAGRANCE GENERATION DEVICE (71) Applicant: SHISEIDO COMPANY, LTD., Tokyo (JP)

(72) Inventors: Yasuhiro Take, Tokyo (JP); Kaoru Matsumoto, Kanagawa (JP); Yuka Nago, Tokyo (JP); Masaki Hanahara, Tokyo (JP); Yuta Manaka, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 42 days.

(21) Appl. No.: 16/491,890

(22) PCT Filed: Mar. 9, 2017

(86) PCT No.: PCT/JP2017/009544
§ 371 (c)(1),
(2) Date: Sep. 6, 2019

(87) PCT Pub. No.: WO2018/163366
PCT Pub. Date: Sep. 13, 2018

(65) Prior Publication Data
US 2020/0009285 A1   Jan. 9, 2020

(51) Int. Cl.
*A61L 9/14* (2006.01)

(52) U.S. Cl.
CPC ............ *A61L 9/14* (2013.01); *A61L 2209/11* (2013.01); *A61L 2209/132* (2013.01); *A61L 2209/133* (2013.01)

(58) Field of Classification Search
None
See application file for complete search history.

(56) References Cited

U.S. PATENT DOCUMENTS

| 7,718,119 B2 | 5/2010 | Tajima et al. |
| 7,934,703 B2 | 5/2011 | Tomono et al. |

FOREIGN PATENT DOCUMENTS

| JP | H06-007714 A | 1/1994 |
| JP | H06-018061 A | 1/1994 |
| JP | 10085315 A * | 4/1998 |

(Continued)

OTHER PUBLICATIONS

Kujirada, M. JPH10-85315A—translated document (Year: 1998).*

(Continued)

*Primary Examiner* — Jelitza M Perez
(74) *Attorney, Agent, or Firm* — Morgan, Lewis & Bockius LLP (57) ABSTRACT

An accurately mixed fragrance can be provided. A fragrance generation device includes: a first ultrasonic vibrator provided in a water container that contains water and used for atomizing the water; a first emission hole used for emitting the water atomized by the first ultrasonic vibrator; a plurality of second ultrasonic vibrators provided in a plurality of perfume containers that individually contain multiple types of perfumes, respectively, and used for atomizing the perfumes; a plurality of second emission holes arranged around the first emission hole and used for emitting the perfumes atomized by the plurality of second ultrasonic vibrators; and a control unit configured to control driving of the first ultrasonic vibrator and the second ultrasonic vibrators.

20 Claims, 10 Drawing Sheets

(56) References Cited

FOREIGN PATENT DOCUMENTS

| | | | |
|---|---|---|---|
| JP | H10-085315 | A | 4/1998 |
| JP | 2002-119584 | A | 4/2002 |
| JP | 2002119584 | A * | 4/2002 |
| JP | 2002-288348 | A | 10/2002 |
| JP | 2003-038630 | A | 2/2003 |
| JP | 2007-000651 | A | 1/2007 |
| JP | 2012-130903 | A | 7/2012 |
| JP | 2012-249818 | A | 12/2012 |
| JP | 2013-158600 | A | 8/2013 |
| JP | 2016-097208 | A | 5/2016 |
| WO | 01/89590 | A1 | 11/2001 |
| WO | 2006/095816 | A1 | 9/2006 |
| WO | 2008-072744 | A1 | 6/2008 |

OTHER PUBLICATIONS

JPH10-85315A—translated document (Year: 1998).*
Nohara, H. JP2002119584A—translated document (Year: 2002).*
Hanahara Masaki, BliScent [online], YouTube, Dec. 14, 2016, [retrieved on May 1, 2017], Retrieved from the Internet: <URL:https://www.youtube.com/watch?v=CJpnenz7kZQ&feature=youtu.be>.
BliScent [online], Dec. 14, 2016, [retrieved on May 1, 2017], Retrieved from the Internet:<URL:https//www.bliscent.net/#new-page>.
International Search Report (with partial translation) and Written Opinion issued in corresponding International application No. PCT/JP2017/009544, dated May 16, 2017.

* cited by examiner

FRAGRANCE GENERATION DEVICE

TECHNICAL FIELD

The present invention relates to a fragrance generation device.

BACKGROUND ART

Devices that diffuse a perfume such as an aroma oil in a space are known. Patent Literature 1 discloses a fragrance preparation device that provides a fragrance mixed in accordance with a preference of the user. This fragrance preparation device may have a plurality of cartridges that can contain different types of perfumes and control the emission amount. The perfume emitted from the cartridges is absorbed in an absorber arranged to face the cartridges and volatilized and diffused by a ventilator.

CITATION LIST

Patent Literature

PTL 1: Japanese Patent Application Laid-Open No. H6-18061

SUMMARY OF INVENTION

Technical Problem

The fragrance preparation device of Patent Literature 1 can control the emission amount of a perfume from cartridges in accordance with a designated mixing ratio. However, since the volatilities of perfumes are different for respective types, it is difficult to control the volatilizing amounts of perfumes from an absorber and provide an accurately mixed fragrance.

The present invention has been made in view of such a problem and intends to provide a fragrance generation device that can provide an accurately combined fragrance.

Solution to Problem

A fragrance generation device according to one embodiment of the present invention includes: a first ultrasonic vibrator provided in a water container that contains water and used for atomizing the water; a first emission hole used for emitting the water atomized by the first ultrasonic vibrator; a plurality of second ultrasonic vibrators provided in a plurality of perfume containers that individually contain multiple types of perfumes, respectively, and used for atomizing the perfumes; a plurality of second emission holes arranged around the first emission hole and used for emitting the perfumes atomized by the plurality of second ultrasonic vibrators; and a control unit configured to control driving of the first ultrasonic vibrator and the second ultrasonic vibrators.

A fragrance generation device according to one embodiment of the present invention includes: a plurality of perfume containers that individually contain multiple types of perfumes, respectively; a plurality of ultrasonic vibrators provided in the plurality of perfume containers, respectively, and used for atomizing the perfumes; and a control unit configured to determine drive periods of the plurality of ultrasonic vibrators in a predetermined cycle individually based on the mixing information.

Advantageous Effects of Invention

According to the present invention, a fragrance generation device that can provide an accurately mixed fragrance is provided.

DESCRIPTION OF EMBODIMENTS

First Embodiment

Figure 1:
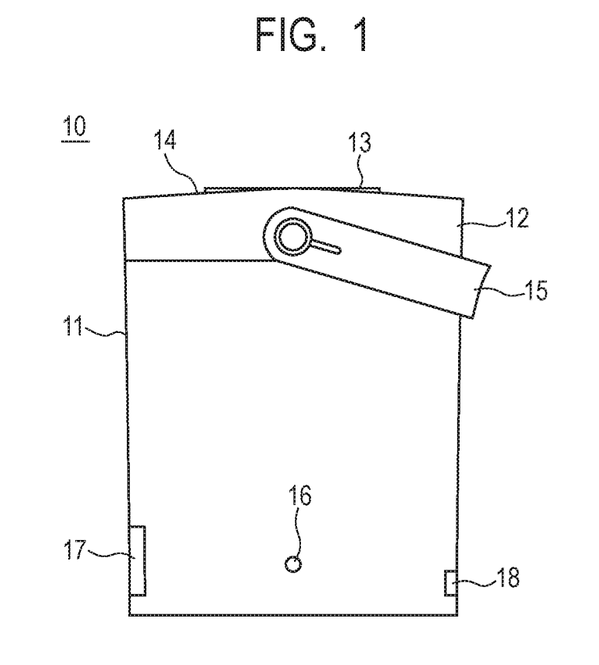
FIG. 1 is a side view of a fragrance generation device according to a first embodiment.
Figure 2:
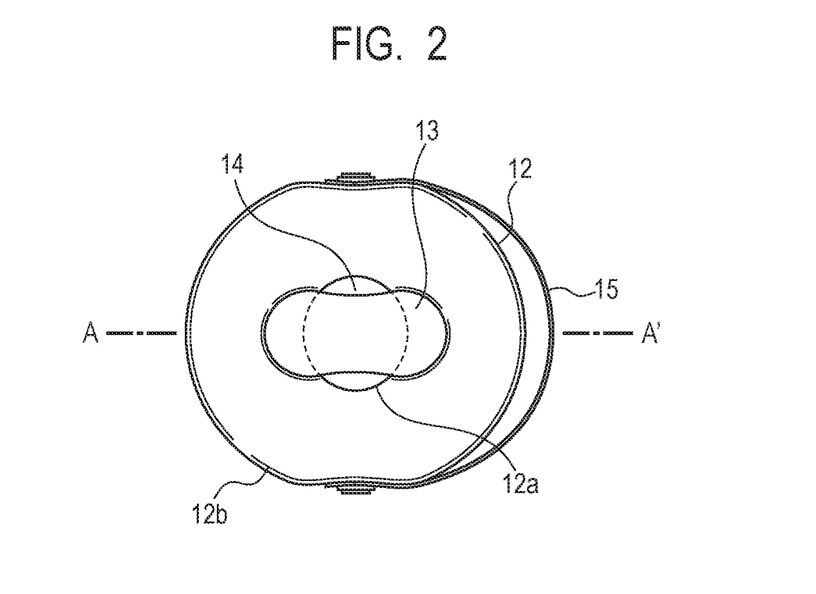
FIG. 2 is a top view of the fragrance generation device according to the first embodiment.
Figure 3:
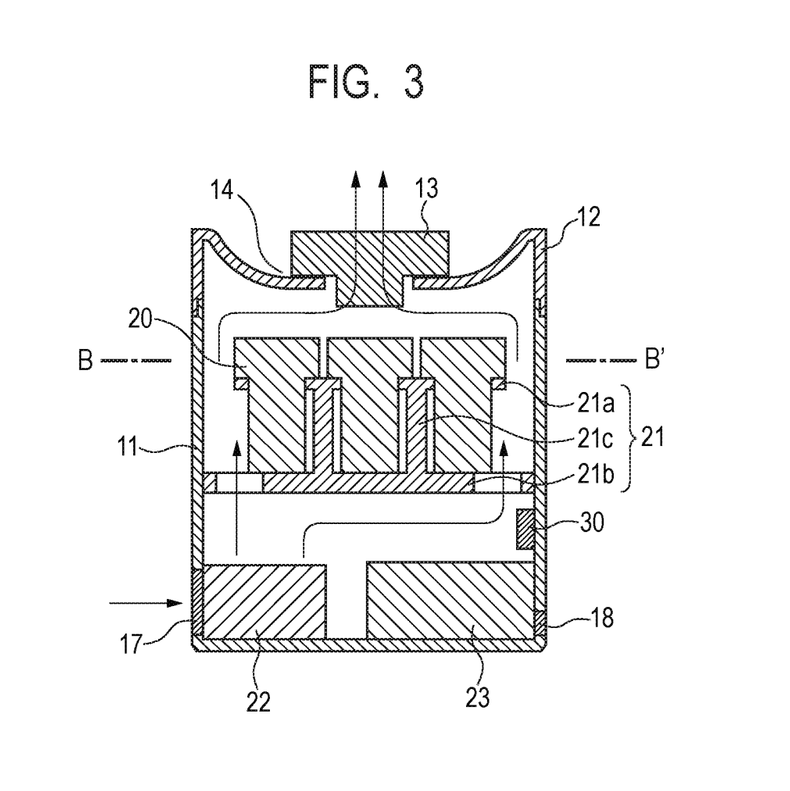
FIG. 3 is a sectional view taken along a line A-A' of FIG. 2.
Figure 4:
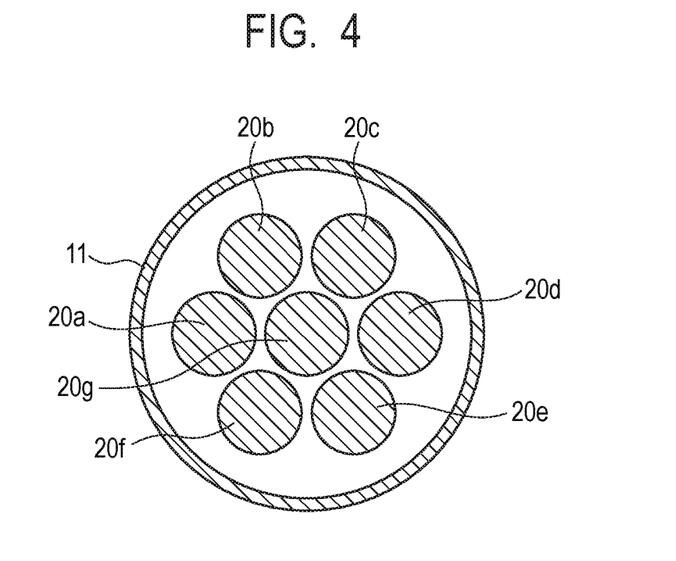
FIG. 4 is a sectional view taken along a line B-B' of FIG. 3.

FIG. 1 is a side view of a fragrance generation device 10 according to the present embodiment. FIG. 2 is a top view of the fragrance generation device 10 according to the present embodiment. Further, FIG. 3 is a sectional view taken along a line A-A' of FIG. 2, and FIG. 4 is a sectional view taken along a line B-B' of FIG. 3. As illustrated in FIG. 1 and FIG. 2, the fragrance generation device 10 has a casing 11, a top cover 12, a lid 13, an atomization hole 14, a handle 15, a light emitting diode (LED) 16, an intake hole 17, and a power supply connection portion 18. Further, as illustrated in FIG. 3 and FIG. 4, the fragrance generation device 10 has a plurality of cartridges 20 (20a to 20g), a storage plate 21, a fan 22, a battery 23, and a control circuit board 30 inside the casing 11. The fragrance generation device 10 atomizes perfumes contained in the plurality of cartridges 20 in accordance with designated mixing information and diffuses the atomized perfumes in a space such as a room.

The casing 11 has a cylindrical shape with a bottom and is formed of a synthetic resin such as an Acrylonitrile Butadiene Styrene (ABS) resin, for example. The top cover 12 and the lid 13 are provided in a removable manner on the upper part of the casing 11. By removing the top cover 12 and the lid 13, it is possible to replace the cartridge 20 easily. The top cover 12 and the lid 13 are formed of a synthetic resin such as an ABS resin as with the casing 11.

The top cover 12 is a disc-shaped member and is fit to and integrated with the casing 11. The top face of the top cover 12 is recessed in a doom shape, and a circular opening 12a is formed in the recessed bottom. An edge 12b of the top cover 12 rises so as to surround the lid 13. The lid 13 is an elliptical plate-shaped member and is placed so as to cross over the opening 12a. The center part of the lid 13 is slightly narrower in the longer axis direction. The longer axis of the lid 13 is longer than the diameter of the opening 12a, and the shorter axis of the lid 13 is shorter than the diameter of the opening 12a. A cylindrical protrusion having a smaller diameter than the opening 12a is formed on the underside of the lid 13. The atomization hole 14 is a space between the top cover 12 and the lid 13 and is located on both sides of the lid 13. The atomization hole 14 is used for emitting the perfume atomized inside the casing 11 to the outside of the fragrance generation device 10. Note that the shape and the arrangement of the top cover 12, the lid 13, and the atomization hole 14 are not limited to the illustrated example.

The handle 15 is an ark-shaped member along the outer circumference of the casing 11 and is formed of a leather, a synthetic resin, or the like, for example. Both ends of the handle 15 are attached in the upper part of the side face of the casing 11 so as to be able to rotate, respectively, and the user is able to carry the fragrance generation device 10 at will by holding the handle 15. The user may change the installation place of the fragrance generation device 10 in accordance with a living scene such as in a living room, a study, a bedroom, or the like, for example.

The LED 16 is provided in the lower part of the side face of the casing 11 and is used for indicating the state of being powered on or off of the fragrance generation device 10. The intake hole 17 is provided in the lower part of the side face of the casing 11 and is used for taking an air into the casing 11. The shape, the arrangement, the number, or the like of intake holes 17 is not particularly limited. A grid member for preventing entry of a foreign material may be provided in the intake hole 17.

The power supply connection portion 18 is provided in the lower part of the side face of the casing 11 and used for charging the battery 23. The power supply connection portion 18 has a micro Universal Serial Bus (USB) terminal, for example, and can receive power supply from an external device connected via the USB cable.

Each of the cartridges 20 has a cylindrical shape and contains a liquid perfume therein. The storage plate 21 can store the plurality of cartridges 20 and is provided in the center part inside the casing 11. The storage plate 21 is formed of a synthetic resin or the like and has a top plate 21a, a bottom plate 21b, and a connection member 21c. The top plate 21a and the bottom plate 21b are circular members arranged so as to face each other in the horizontal direction and are connected by the connection member 21c to each other. The bottom plate 21b is fixed to the inner wall of the casing 11, and the connection member 21c supports the top plate 21a from the bottom side. A plurality of holding holes each having substantially the same diameter as the cartridge 20 are formed in the top plate 21a, and the cartridge 20 is placed on the bottom plate 21b while being inserted in the holding hole. The cartridge 20 is able to easily removed from the storage plate 21.

The number of cartridges 20 stored in the storage plate 21 is not particularly limited, and different types of perfumes may be contained in the plurality of cartridges 20. Instead of a perfume, water may be contained in the cartridge 20. For example, as illustrated in FIG. 4, seven cartridges 20a to 20g are stored in the storage plate 21. In the present embodiment, in a plan view, water is contained in the cartridge 20g arranged at the center of the casing 11, and different types of perfumes are contained in six cartridges 20a to 20f arranged around the cartridge 20g, respectively. In the following description, perfumes contained in the cartridges 20a to 20f are referred to as perfumes A to F, respectively.

The fan 22 is a propeller fan, a sirocco fan, a turbo fan, or the like, for example, and has an impeller and a motor unit. The fan 22 is arranged near the intake hole 17 in the bottom inside the casing 11 and sends out a sucked air upward via the intake hole 17.

In the bottom plate 21b provided above the fan 22, flow paths 21d are formed along the inner wall of the casing 11, and the air from the fan 22 flows into the periphery of the cartridges 20 through the flow paths 21d. The inflow air rises in the space between the casing 11 and the cartridges 20, is guided to a part under the lid 13 along the underside of the top cover 12, and is exhausted from the atomization hole 14. The perfume (or water) inside the cartridge 20 is carried on the airflow, emitted from the atomization hole 14, and diffused to the peripheral space.

The battery 23 is a rechargeable battery such as a lithium ion battery, a nickel hydrogen battery, or the like, for example, and outputs predetermined DC power. The battery 23 is arranged near the power supply connection portion 18 in the bottom inside the casing 11 and charged by an external power supply connected via the power supply connection portion 18. The battery 23 may be configured to be charged by contactless wireless powering without intervention of the power supply connection portion 18.

The control circuit board 30 is electrically connected to the cartridges 20, the fan 22, the battery 23, the LED 16, and the like via wirings (not illustrated). Various electronic circuits for driving or controlling each component of the fragrance generation device 10 are implemented on the control circuit board 30. Note that the fragrance generation device 10 may be provided with a power button used for turning on or off the power supply from the battery 23, a speaker used for outputting a background music (BGM) in accordance with mixing information on a perfume, or the like.

Figure 5:
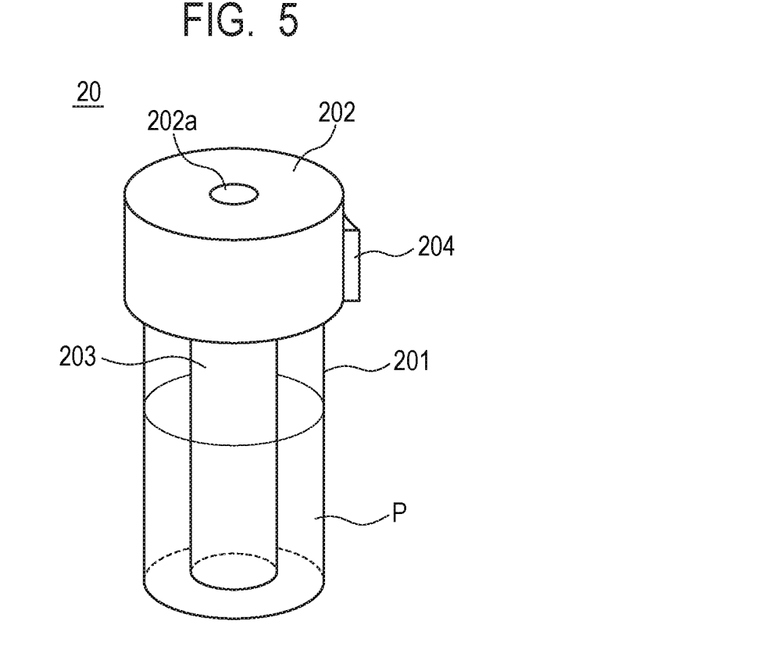
FIG. 5 is a perspective view of a cartridge according to the first embodiment.
Figure 6:
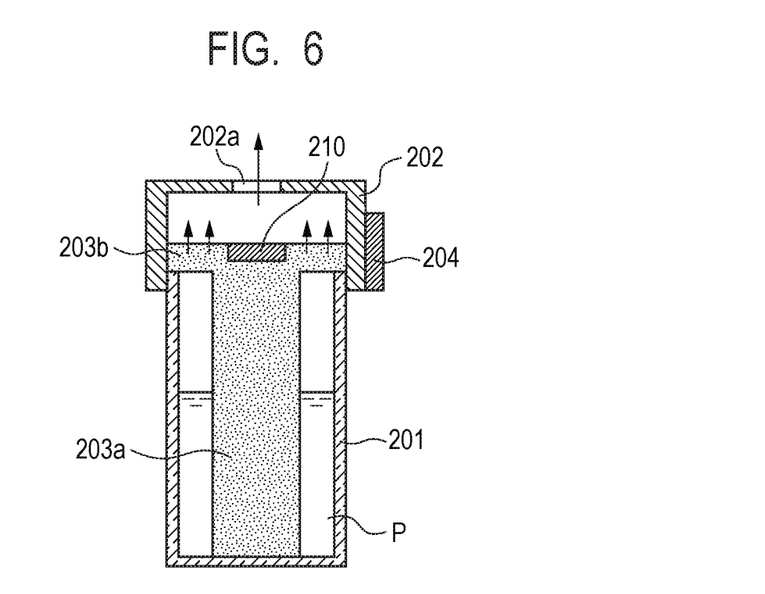
FIG. 6 is a sectional view of the cartridge according to the first embodiment.

Next, the cartridge 20 will be described in detail. FIG. 5 is a perspective view of the cartridge 20 according to the present embodiment. FIG. 6 is a sectional view of the cartridge 20 according to the present embodiment. The cartridge 20 has a perfume container 201, a vibrator case 202, a liquid absorption member 203, a connection portion 204, and an ultrasonic vibrator 210.

The perfume container 201 has a cylindrical shape with a bottom and is formed of a transparent glass or the like, for example. A liquid perfume P is contained inside the perfume container 201. The perfume P may be an undiluted solution of a perfume or may be one in which a solid or liquid perfume is solved in an organic solvent. Alternatively, it may be a liquid whose viscosity is increased by adding a thickener or a gelling agent to the above. The perfume P is an essential oil, a fragrance oil, or the like, for example, and is not particularly limited as long as it is a liquid including an aroma component.

The vibrator case 202 is provided in the upper part of the perfume container 201. The vibrator case 202 has a cylindrical shape whose top part is closed and is formed of a synthetic resin or the like, for example. The inner diameter of the vibrator case 202 is substantially the same as the outer diameter of the perfume container 201, and the upper part of the perfume container 201 is closed by the vibrator case 202. The vibrator case 202 may be fixed to the perfume container 201 or may be removable from the perfume container 201. A circular emission hole 202a is formed at center of the upper side of the vibrator case 202.

The ultrasonic vibrator 210 and a part of the liquid absorption member 203 (diffusion portion 203b) are contained in the vibrator case 202. The cross section in the perpendicular direction of the liquid absorption member 203 is a T-shape, and the liquid absorption member 203 includes a cylindrical suction portion 203a formed in the lower part and a disc-shaped diffusion portion 203b formed in the upper part. The suction portion 203a is used for sucking the perfume P up to the diffusion portion 203b by utilizing a capillary phenomenon and is formed of a porous material having a rich liquid absorption property, such as a non-woven fabric, a felt, a sponge, or the like, for example. The lower end of the suction portion 203a is arranged so as to come into contact with the inner bottom face of the perfume container 201, and the upper end of the suction portion 203a is connected to the center of the underside of the diffusion portion 203b.

The diffusion portion 203b is integrally formed with the suction portion 203a and absorbs the perfume P from the suction portion 203a. The same material as that of the suction portion 203a can be used for the diffusion portion 203b. A circular recess is provided in the center of the upper side of the diffusion portion 203b, the ultrasonic vibrator 210 is held by the recess. That is, in a top view, the diffusion portion 203b is formed in an annular shape, and the ultrasonic vibrator 210 is arranged at the center part thereof. Note that the shape and the arrangement of the liquid absorption member 203 and the ultrasonic vibrator 210 are not limited to the illustrated example. For example, the liquid absorption member 203 may have a cylindrical shape having a constant diameter, and the annular ultrasonic vibrator 210 may be arranged to surround the liquid absorption member 203 at the upper part of the liquid absorption member 203.

The ultrasonic vibrator 210 is connected to the connection portion 204 via a wiring (not illustrated) and can generate ultrasonic vibration in accordance with a signal from the connection portion 204. The ultrasonic vibration propagates to the diffusion portion 203b, and the perfume P absorbed in the diffusion portion 203b changes to fine particles by the ultrasonic vibration, and the particles are diffused from the surface of the diffusion portion 203b and thus atomized. The atomized perfume P is emitted from the emission hole 202a to the outside of the cartridge 20.

The connection portion 204 is provided on the outer side face of the vibrator case 202 and used for electrically connecting the cartridge 20 to the main unit of the fragrance generation device 10. Specifically, the connection portion 204 is connected to the control circuit board 30 via a wiring (not illustrated) extending from the control circuit board 30. For example, the connection portion 204 has a two-pin female connector, and a two-pin male connector corresponding to the female connector may be provided at the end of the wiring from the control circuit board 30. Further, the connection portion 204 may include an integrated circuit (IC) chip in which an identification (ID) of the cartridge 20, the type of the contained perfume, or the like is stored. The IC chip can also be used for sensing the remaining quantity of the cartridge 20 and, for example, the capacity of the cartridge 20 may be pre-stored in the IC chip, and the remaining quantity of the perfume P can be detected from the emission amount of the perfume P.

Figure 7:
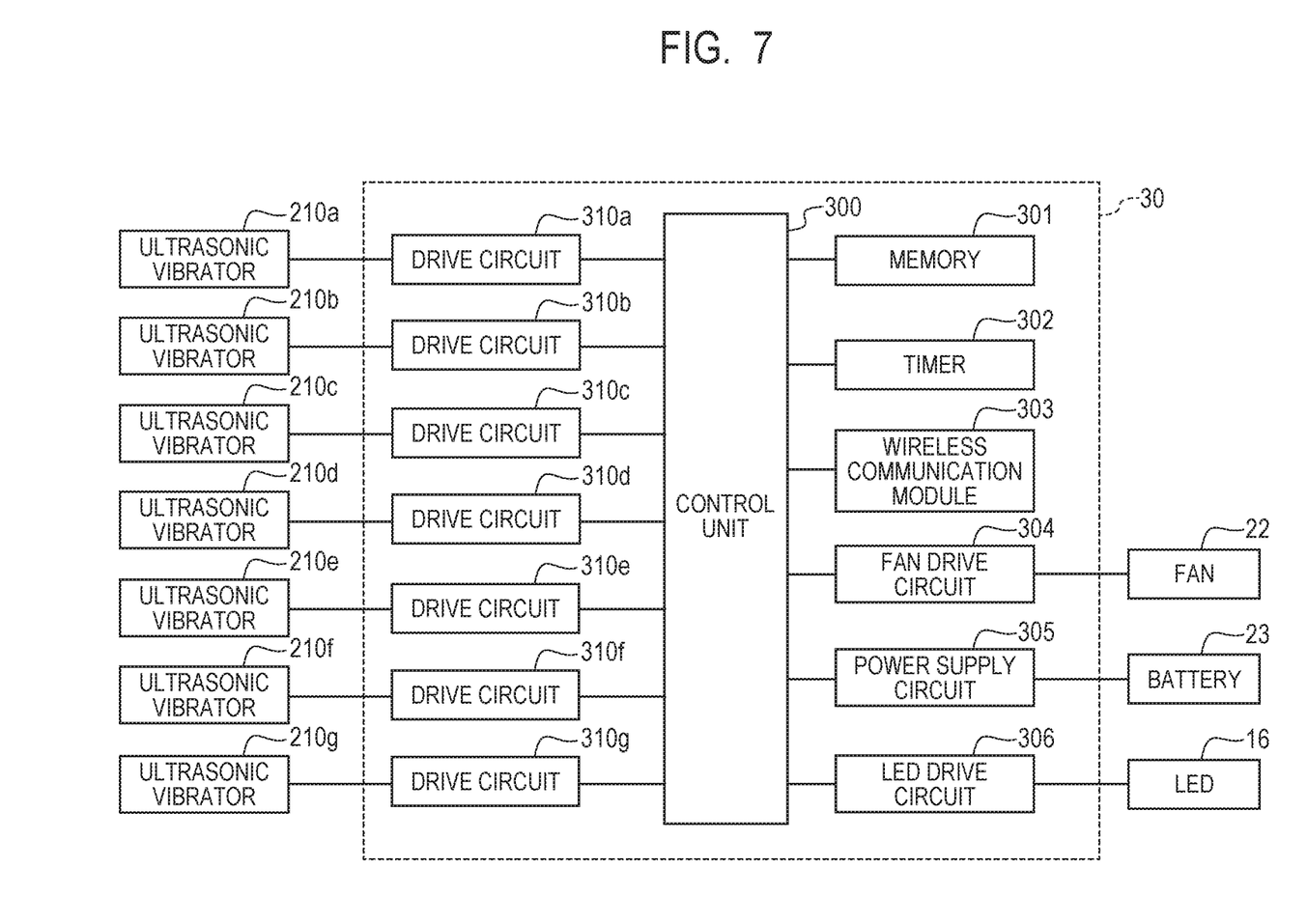
FIG. 7 is a block diagram of the fragrance generation device according to the first embodiment.

FIG. 7 is a block diagram of the fragrance generation device 10 according to the present embodiment. The fragrance generation device 10 has a control unit 300, a memory 301, a timer 302, a wireless communication module 303, a fan drive circuit 304, a power supply circuit 305, an LED drive circuit 306, and a plurality of drive circuits 310 (310a to 310g) on the control circuit board 30.

The control unit 300 includes a central processing unit (CPU), a read only memory (ROM), and a random access memory (RAM) and integrally controls respective components of the fragrance generation device 10. The ROM is formed of a nonvolatile memory and stores a control program executed by the CPU. The control program may be downloaded from a server via a network. The RAM provides a memory field required for the operation of the CPU. The control unit 300 can implement the control of the fragrance generation device 10 by reading and executing a predetermined control program. For example, the control unit 300 can control the operation timing of the plurality of drive circuits 310 based on information pre-stored in the memory 301 or information received from the wireless communication module 303.

The memory 301 is a nonvolatile memory such as a flash memory, for example, and stores mixing information on perfumes, remaining quantity information on the cartridge 20, status information on the fragrance generation device 10, or the like. The mixing information includes the types of perfumes A to F and a mixing ratio. The timer 302 can count an input clock signal and measure elapsed time. The timer 302 may have a plurality of counters that operate independently.

The wireless communication module (wireless communication unit) 303 is an interface for performing wireless communication with an external device. The wireless communication module 303 has an antenna and a transceiver circuit and can establish connection to an external device by using a communication scheme such as Bluetooth (registered trademark), a wireless LAN, or the like. The external device may include a communication terminal such as a smartphone, a tablet computer, or the like or a network server such as a web server. In response to receiving mixing information on perfumes from an external device, the wireless communication module 303 stores the received mixing information in the memory 301. The mixing information may be merely updated or may be stored together with an update history. The wireless communication module 303 can receive various commands (an atomization stop command, a power on/off command, or the like) to provide instructions of the operation of the fragrance generation device 10 in addition to mixing information on perfumes from the external device.

The fan drive circuit 304 is connected to the fan 22 and drives the fan 22 based on a signal from the control unit 300. For example, the fan drive circuit 304 outputs a drive signal to the motor unit of the fan 22, the motor unit rotates the impeller in accordance with drive signal, and the impeller generates an airflow. The power supply circuit 305 has a direct current (DC)-DC converter or a regulator circuit and converts the power of the battery 23 and supplies the converted power to each component of the fragrance generation device 10.

The LED drive circuit 306 is connected to the LED 16 and drives the LED 16 based on a signal from the control unit 300. For example, the LED drive circuit 306 can control the light emission intensity or a lighting pattern of the LED 16 by adjusting a drive current of the LED 16. Note that the LED 16 may include one or more LEDs for rendering in addition to an LED indicating a power supply state. For example, a plurality of LEDs having different light colors may be provided inside the casing 11, and a part of the casing 11 may be transparent or semitransparent, and thereby the LED 16 may have a function of indirect lighting or illumination.

The plurality of drive circuits 310 are connected to the corresponding ultrasonic vibrators 210 and individually drive the ultrasonic vibrators 210 based on a signal from the control unit 300. Each of the ultrasonic vibrators 210 has a plate-shape piezoelectric ceramics and electrodes formed on both faces thereof, for example, and repeats expansion and contraction in response to being applied with a resonance frequency voltage from the corresponding drive circuit 310 to generate ultrasonic vibration. For example, the frequency of the ultrasonic vibration is 1 MHz to 3 MHz, and the average particle diameter of a perfume P and water atomized by the ultrasonic vibration is around 1 μm to 10 μm.

Figure 8:
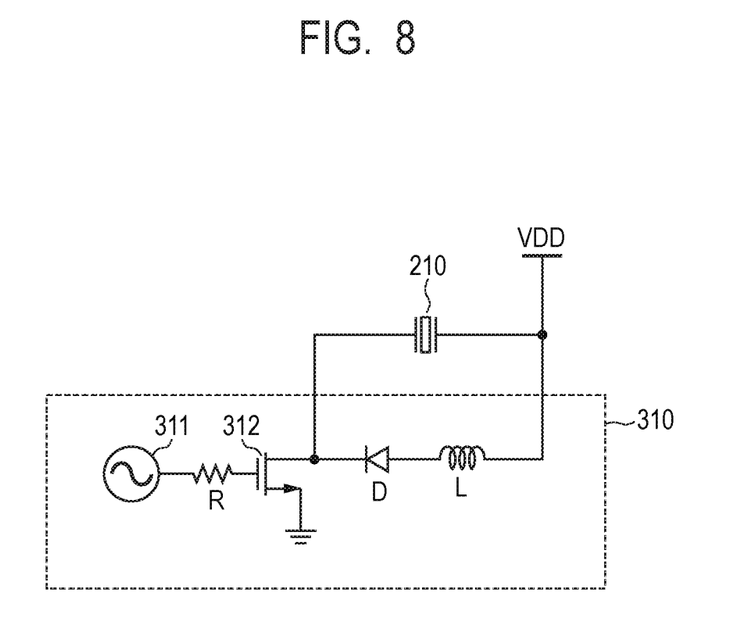
FIG. 8 is a circuit diagram of a drive circuit according to the first embodiment.

Next, details of the configuration and the operation of the drive circuit 310 will be described. FIG. 8 is a circuit diagram of the drive circuit 310. The drive circuit 310 has an oscillator 311, a Metal Oxide Semiconductor (MOS) transistor 312, a resistor R, a diode D, and a coil L. The gate terminal of the MOS transistor 312 is connected to the oscillator 311 via the resistor R, and the source terminal of the MOS transistor 312 is grounded. The drain terminal of the MOS transistor 312 is connected to a voltage source VDD via the diode D and the coil L arranged in series. The ultrasonic vibrator 210 is connected in parallel to the diode D and the coil L.

The oscillator 311 generates a voltage signal at the resonance frequency of the ultrasonic vibrator 210 and inputs the voltage signal to the gate terminal of the MOS transistor 312 via the resistor R. In response to the MOS transistor 312 being turned on by the voltage signal from the oscillator 311, a current from the voltage source VDD flows through the coil L. In response to the MOS transistor 312 being turned off, a voltage is excited in the coil L, and the energy flowing in a conduction direction of the diode D and accumulated in the coil L is transferred to the ultrasonic vibrator 210. That is, a higher voltage than the voltage of the voltage source VDD is applied to the ultrasonic vibrator 210. Since the diode D blocks a reverse current from the ultrasonic vibrator 210, a state where the high voltage is applied to the ultrasonic vibrator 210 is maintained until the MOS transistor 312 is next turned on. In such a way, it is possible to drive the ultrasonic vibrator 210 by a switching operation of the MOS transistor 312. Note that the configuration of the drive circuit 310 is not limited to the illustrated example.

Figure 9:
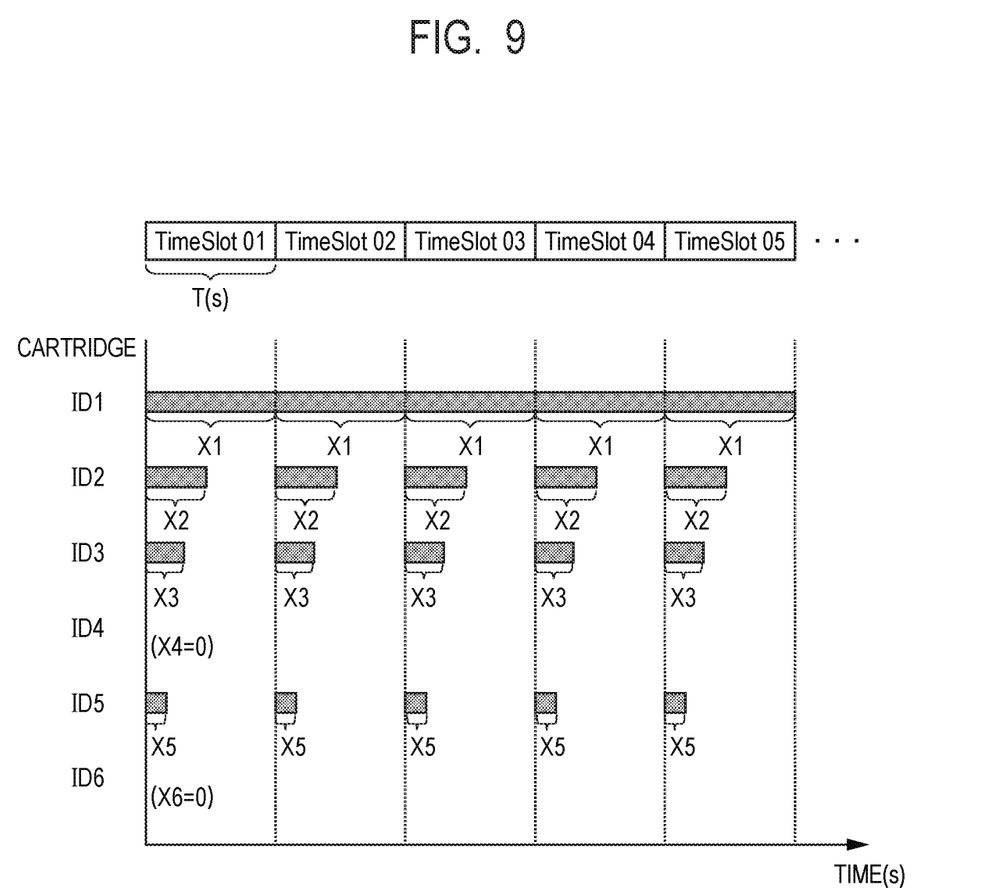
FIG. 9 is a conceptual view illustrating drive control of an ultrasonic vibrator according to the first embodiment.

FIG. 9 is a conceptual diagram illustrating drive control of the ultrasonic vibrator 210 according to the present embodiment and illustrates one example of an atomization operation of each cartridge from timeslot 01 to timeslot 05. In FIG. 9, the horizontal axis represents time, and the vertical axis represents cartridges ID1 to ID6. The ID1 to ID6 are respective identification numbers of the cartridges 20a to 20f. A timeslot is a periodical time span, and a cycle T of the timeslot is predefined. Operation periods X1 to X6 of respective cartridges for each timeslot are determined in accordance with mixing information on perfumes. For example, when the mixing ratio of the perfumes A to F is 6:3:2:0:1:0, the operation periods X1 to X6 of the cartridges 20a to 20f are determined to be 6 seconds, 3 seconds, 2 seconds, 0 second, 1 second, and 0 second, respectively. Note that while the cycle T=6 seconds in the present embodiment, the cycle T may be any length such as 10 seconds, 30 seconds, 60 seconds, or the like without being limited to the above.

At time 0, that is, the start time of timeslot 01, all the cartridges ID1 to ID6 start atomization. Each cartridge suspends the atomization after the operation period elapses from the start of atomization. Since the operation time X1 of the cartridge ID1 is the same as the cycle T of the timeslot, the cartridge ID1 performs atomization without being suspended as a result. Further, since the operation periods X4 and X6 of the cartridges ID4 and ID6 are 0 seconds, the cartridges ID4 and ID6 do not perform atomization as a result. Also at the start of the next timeslot 02, all the cartridges ID1 to ID6 start atomization (the cartridges ID4 and ID6 do not perform atomization), and each cartridge suspends the atomization after the operation period elapses from the start of atomization. Similarly, in the subsequent timeslots, the cartridges ID1 to ID6 intermittently repeat atomization operations.

Figure 10:
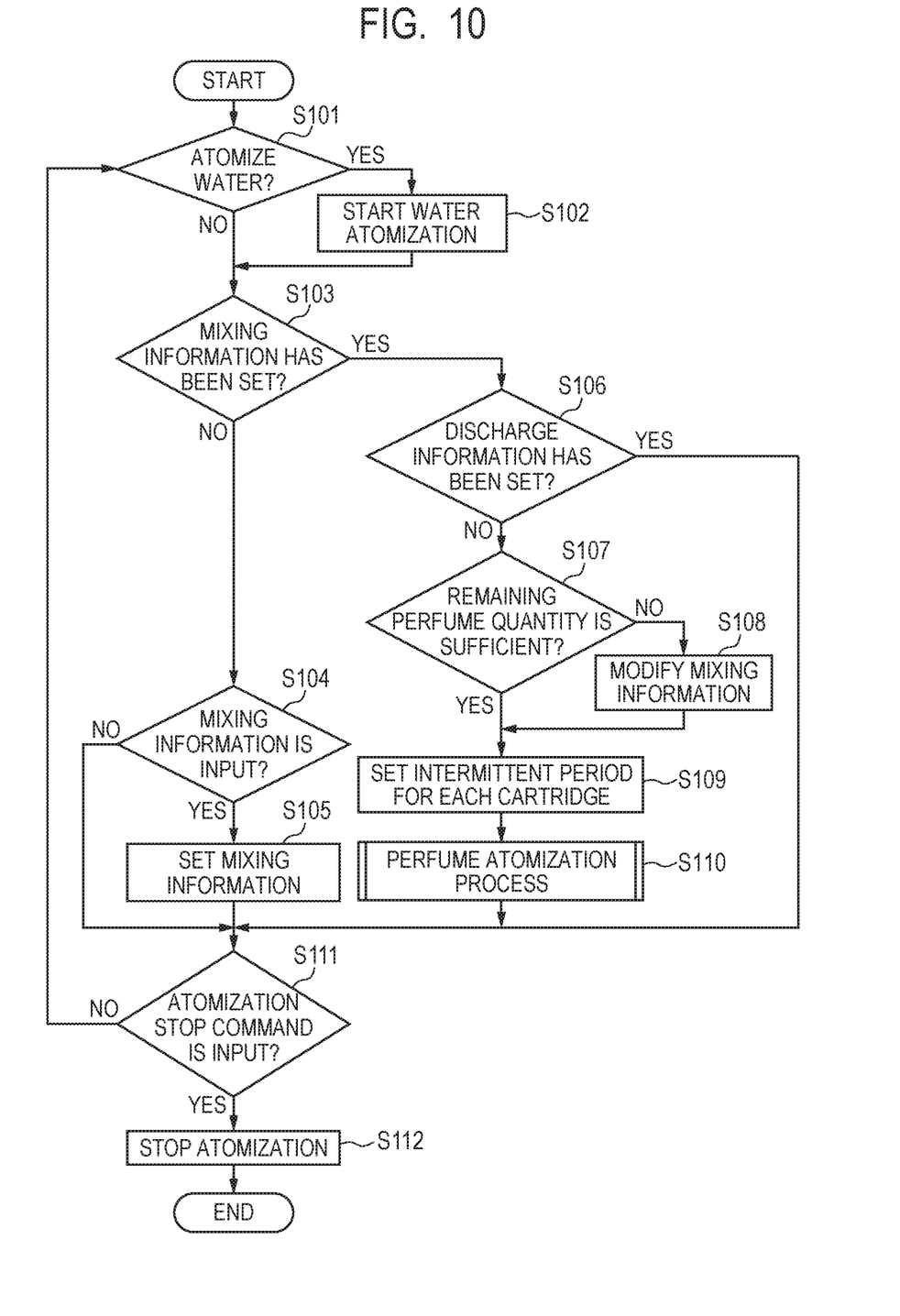
FIG. 10 is a flowchart illustrating the operation of the fragrance generation device according to the first embodiment.

FIG. 10 is a flowchart illustrating the process in the fragrance generation device 10 according to the present embodiment. First, once the fragrance generation device 10 is powered on in response to a user operation or a command from an external device, the control unit 300 starts the process of the flowchart of FIG. 10.

First, the control unit 300 reads setting information stored in the memory 301 and determines whether or not to atomize water (step S101). If it is set to atomize water (step S101, YES), the control unit 300 identifies the cartridge 20g containing water and starts an operation of the cartridge 20g (step S102). That is, the control unit 300 continuously drives the ultrasonic vibrator 210g via the drive circuit 310g. Atomization of water is continued to be performed until it is set not to atomize water. If it is set not to atomize water (step S101, NO), the control unit 300 determines whether or not mixing information on perfumes is set (step S103). That is, the control unit 300 determines whether or not mixing information on perfumes is stored in the memory 301.

If no mixing information on perfumes is set (step S103, NO), the control unit 300 determines whether or not mixing information is input from an external device via the wireless communication module 303 (step S104). The mixing information here may be received in a predetermined format such as "S632010E", for example. The symbols "S" and "E" denote start and end of data, and six numbers between "S" and "E" denote mixing ratio of the perfumes A to F.

If mixing information is input (step S104, YES), the control unit 300 sets the mixing information in the memory 301 (step S105). That is, the control unit 300 identifies the cartridges 20a to 20f containing the perfumes A to F based on the mixing information and stores respective operation periods associated with the cartridges 20a to 20f in the memory 301. After setting the mixing information, the control unit 300 determines whether or not an atomization stop command is input from an external device via the wireless communication module 303 (step S111). Further, if no mixing information is input (step S104, NO), the control unit 300 proceeds to step S111 to determine whether or not an atomization stop command is input.

If mixing information on perfumes has been set (step S103, NO), the control unit 300 determines whether or not discharge information has been set (step S106). That is, the control unit 300 determines whether or not discharge information is stored in the memory 301. The discharge information may include a flag indicating that atomization of perfumes is ongoing, information on the remaining quantity of perfumes, or the like.

If no discharge information is set (step S106, YES), the control unit 300 uses the mixing information and the discharge information to determine whether or not the remaining quantity of perfumes is sufficient (step S107). That is, the control unit 300 predicts temporal change in the remaining quantity of each perfume resulted when atomization is performed in accordance with mixing information and determines whether or not it is possible to continue atomization for a predetermined period (for example, one to two hours). If the remaining quantity of perfumes is short (step S107, NO), the control unit 300 modifies the mixing information (step S108). For example, the control unit 300 reduces the mixing ratio of the type of perfume whose remaining quantity is predicted to become zero before the predetermined period elapses. If the remaining quantity of perfumes is not short (step S107, YES), the control unit 300 does not modify the mixing information.

Subsequently, the control unit 300 sets an intermittent period of each cartridge (step S109). As illustrated in FIG. 9, the control unit 300 sets a timeslot of the cycle T and determines a timing of start of an operation and end of the operation of the cartridges 20a to 20f in each timeslot. The control unit 300 starts counting time by the timer 302, drives the ultrasonic vibrators 210a to 210f via the drive circuits 310a to 310f, and performs a perfume atomization process (step S110). If discharge information on perfumes has been set (step S106, YES), the control unit 300 continues the perfume atomization process (step S110) until an atomization stop command is input at step S111.

If an atomization stop command is input (step S111, YES), the control unit 300 stops atomization of all the water and the perfumes (step S112). That is, the control unit 300 stops driving of the ultrasonic vibrators 210a to 210g via the drive circuits 310a to 310g. The control unit 300 turns off the LED 16 and powers off the fragrance generation device 10. Note that the control unit 300 may stop driving all the ultrasonic vibrators 210a to 210g also when the remaining quantity of any one of the cartridges 20a to 20g becomes zero.

Figure 11:
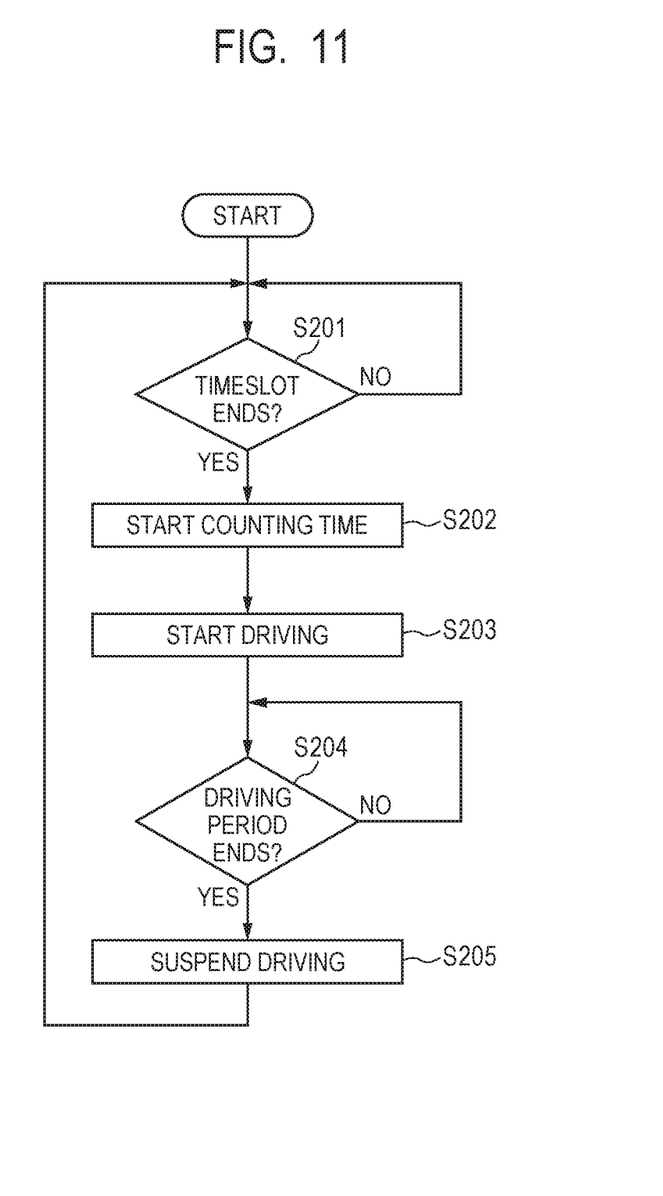
FIG. 11 is a flowchart illustrating the detail of an atomization process according to the first embodiment.

FIG. 11 is a flowchart illustrating the detail of the atomization process according to the present embodiment. First, the control unit 300 determines whether or not the current timeslot has ended (step S201). For example, when the cycle T of the timeslot is 6 seconds, the control unit 300 determines whether or not 6 seconds have elapsed from the start of counting time. If the timeslot has not yet ended (step S201, NO), the control unit 300 stands by until the timeslot ends. If the timeslot has ended (step S201, YES), the control unit 300 newly starts counting time by using the timer 302 (step S202). That is, in the next timeslot, elapsed time from the start time of the timeslot is measured by the timer 302. Subsequently, the control unit 300 starts driving the ultrasonic vibrators 210a to 210g (step S203). The control unit 300 does not drive an ultrasonic vibrator for which the drive period is set to 0 second.

Next, the control unit 300 determines whether or not a drive period of the ultrasonic vibrator 210 being driven has ended (step S204). That is, the control unit 300 determines whether or not the elapsed time in the current timeslot exceeds the drive period of the ultrasonic vibrator 210. For example, when the drive period of the ultrasonic vibrators 210a to 210f are 6 seconds, 3 seconds, 2 seconds, 0 second, 1 second, and 0 second, respectively, the control unit 300 determines whether or not 1 second, 2 seconds, and 3 seconds have elapsed from the start of counting time. Here, for the ultrasonic vibrator 210a for which the drive period is set to 6 seconds (that is, the same as the cycle T), a drive period determination process (step S204) and a drive suspension process described later (step S205) can be omitted.

If the drive period has not yet ended (step S204, NO), the control unit 300 stands by until the drive period ends. If at least one drive period of the ultrasonic vibrators 210 being driven has ended (step S204, NO), the control unit 300 suspends the driving of the ultrasonic vibrator 210 for which the drive period has ended via the corresponding drive circuit 310 (step S205). For example, the control unit 300 suspends the driving of the ultrasonic vibrator 210e when 1 second has elapsed from the start of counting time, suspends the driving of the ultrasonic vibrator 210c when 2 seconds have elapsed from the start of counting time, and suspends the driving of the ultrasonic vibrator 210b when 3 seconds have elapsed from the start of counting time. The control unit 300 returns to step S201 and repeats the process of steps S202 to S205 for the next timeslot.

In the present embodiment, the cartridge 20g containing water is arranged at the center of the fragrance generation device 10, and the plurality of cartridges 20a to 20f containing different types of perfumes are arranged in the periphery thereof. The ultrasonic vibrators 210a to 210f are provided in the cartridges 20a to 20f, respectively, and a drive period and a suspension period are set within a timeslot based on a mixing ratio of perfumes. The amount of a perfume atomized from each cartridge is proportional to a drive period of an ultrasonic vibrator, and the atomized perfume is mixed evenly in the space inside the casing 11 and emitted outward from the atomization hole 14 due to an airflow from the fan 22. Thereby, the fragrance that is mixed accurately in accordance with the mixing ratio can be provided to the user.

Water contained in the cartridge 20g is always atomized, and the atomized water is mixed with multiple types of atomized perfumes in the space inside the casing 11 and diffused to the outside of the casing 11 from the atomization hole 14. Since the emission holes 202a of the cartridges 20a to 20f containing multiple types of perfumes are arranged around the emission hole 202a of the cartridge 20g containing water, the multiple types of perfumes can be mixed to the atomized water substantially evenly by the airflow caused by the fan 22. This can improve mixing accuracy.

Furthermore, the temperature around the fragrance generation device 10 is adjusted by atomization of water, and the strength of a fragrance felt by the user can be enhanced. Further, while the size of an atomized perfume particle is different in accordance with the type thereof, variation in the weight of particles floating in the space by mixing atomized water particles and perfume particles can be suppressed, and it is possible to reduce the difference in diffusion speeds that may be caused in accordance with the types of perfumes.

Since atomized water can be easily viewed, it is possible to allow the user to visually recognize generation of a fragrance and improve the effect of the fragrance by atomizing water together with perfumes. Furthermore, the operation of the fragrance generation device 10 can be more easily perceived, and a healing effect caused by a flow or fluctuation of a mist may be expected.

Second Embodiment

While water is contained in the removable cartridge 20g in the fragrance generation device 10 in the embodiment described above, water may be contained in a container fixed to the device main unit. The fragrance generation device 10 in the present embodiment will be described mainly for features different from those of the fragrance generation device 10 in the first embodiment.

Figure 12:
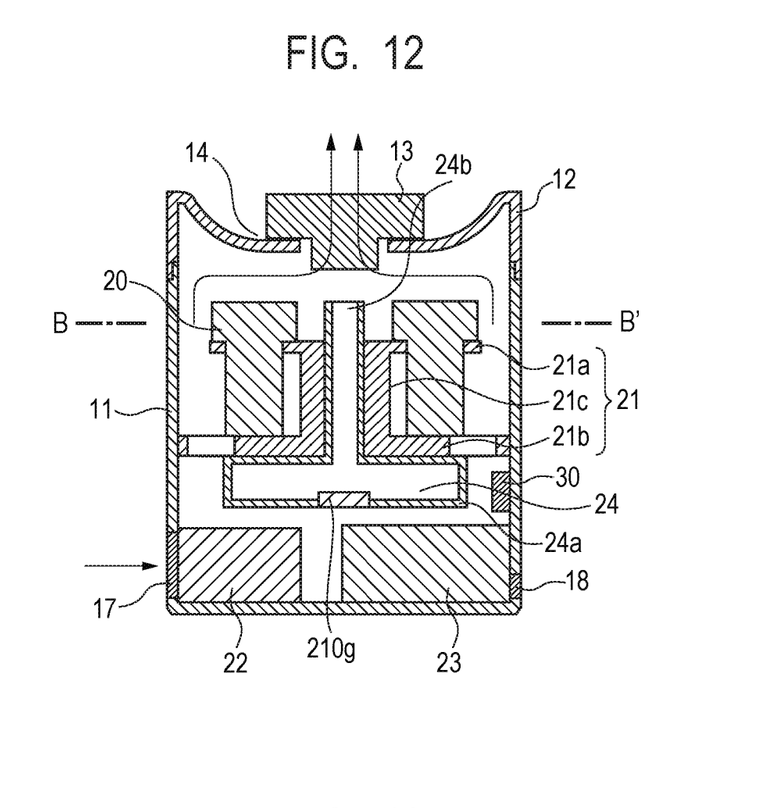
FIG. 12 is a sectional view of a fragrance generation device according to a second embodiment.
Figure 13:
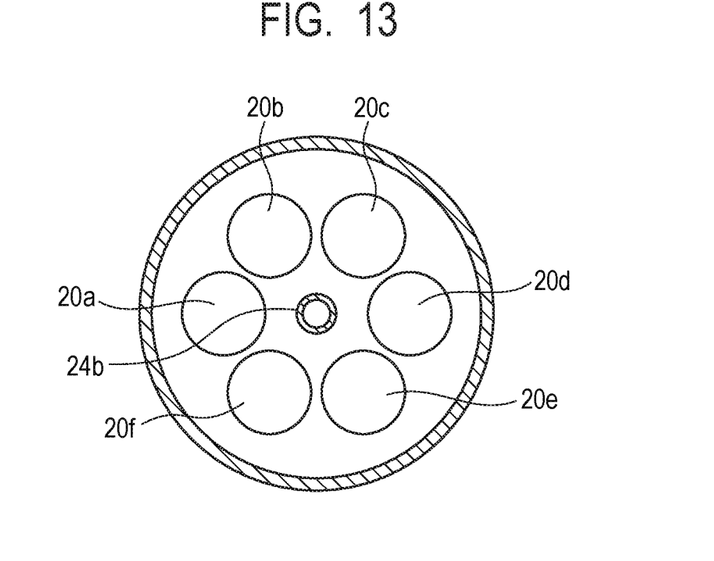
FIG. 13 is a sectional view taken along a line B-B' of FIG. 12.

FIG. 12 is a sectional view of the fragrance generation device 10 according to the present embodiment. FIG. 13 is a sectional view taken along a line B-B' of FIG. 12. The fragrance generation device 10 has the casing 11, the top cover 12, the lid 13, the atomization hole 14, the intake hole 17, the power supply connection portion 18, a plurality of cartridges 20 (20a to 20f), the storage plate 21, the fan 22, the battery 23, a water container 24, and the control circuit board 30.

The water container 24 has a water supply portion 24a, a water storage portion 24b, and the ultrasonic vibrator 210g. The water supply portion 24a has a cylindrical shape and is surrounded by the cartridges 20a to 20f. The top end face of the water supply portion 24a is arranged to be at the same height as the top end face of the cartridges 20a to 20f. The water supply portion 24a serves as a supply hole used for pouring water in the water storage portion 24b and also serves as an emission hole used for emitting water atomized by the water storage portion 24b to the outside of the water container 24. The water storage portion 24b is provided in the lower part of the bottom plate 21b, and the bottom end of the water supply portion 24a penetrates the bottom plate 21b and is connected to the water storage portion 24b.

The water storage portion 24b is a cylindrical container having a bottom and has a larger diameter than the water supply portion 24a. The top face of the water storage portion 24b is closed, and a circular opening is formed at the center of the tope face. The opening is connected to the bottom end of the water supply portion 24a, and the water supply portion 24a and the water storage portion 24b are integrally formed. Note that the entire water container 24 may be integrally formed with the storage plate 21.

The number of cartridges 20 stored in the storage plate 21 is not particularly limited, and different types of perfumes may be contained in the plurality of cartridges 20. For example, as illustrated in FIG. 13, six cartridges 20a to 20f are stored in the storage plate 21. In the present embodiment, in a plan view, water is contained in the water container 24 arranged at the center of the casing 11, and different types of perfumes are contained in six cartridges 20a to 20f arranged around the water container 24, respectively.

The ultrasonic vibrator 210g is provided at the center of the bottom of the water container 24. The ultrasonic vibrator 210g is connected to the control circuit board 30 via a wiring (not illustrated) and can generate ultrasonic vibration in accordance with a signal from the control circuit board 30. Water stored in the water storage portion 24b is changed to fine particles by the ultrasonic vibration, and the particles are diffused from the water surface and thus atomized. The atomized water is discharged from the water supply portion 24a to the outside of the water container 24.

While the water container 24 that contains water is fixed under the cartridges 20a to 20f that contain perfumes in the present embodiment, the emission hole (the water supply portion 24a) of the water container is arranged so as to be surrounded by the emission holes 202a of the cartridges 20a to 20f. Therefore, an accurately mixed fragrance can be provided to the user in the same manner as the first embodiment.

Third Embodiment

Figure 14:
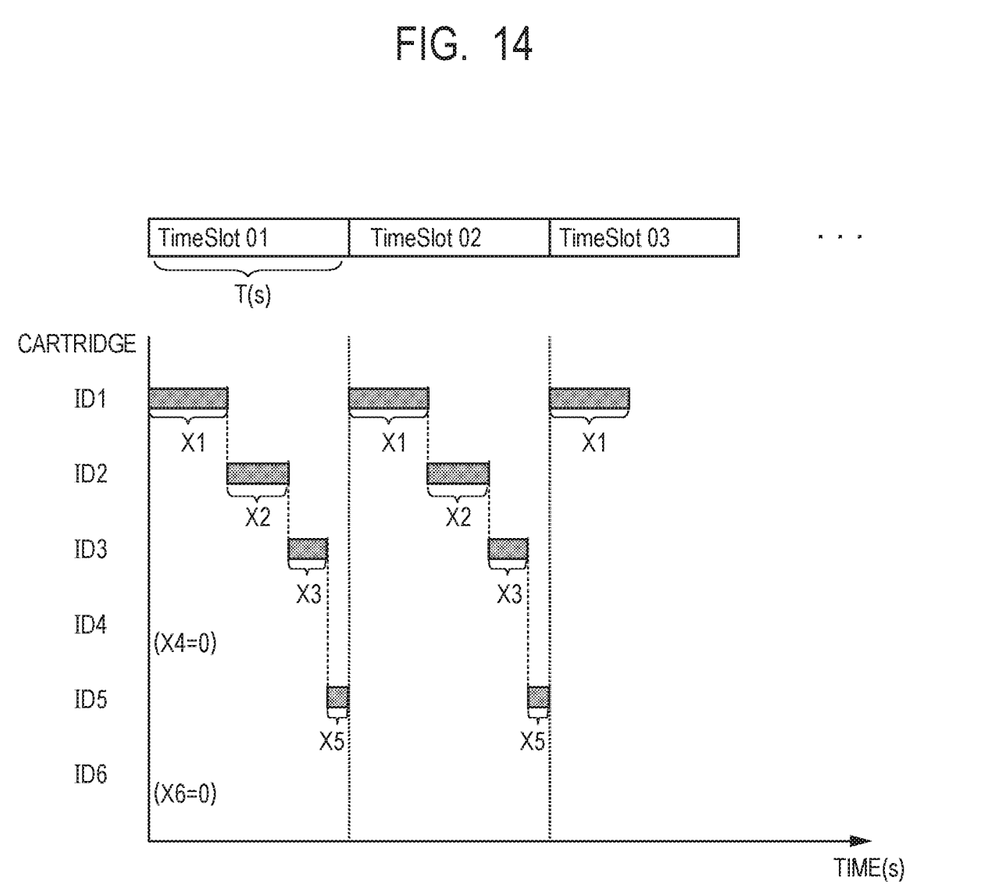
FIG. 14 is a conceptual view illustrating drive control of an ultrasonic vibrator according to a third embodiment.

FIG. 14 is a conceptual diagram illustrating drive control of the ultrasonic vibrator 210 according to the third embodiment and illustrates one example of an atomization operation of each cartridge from timeslot 01 to timeslot 03. The fragrance generation device 10 of the present embodiment drives the ultrasonic vibrators 210 in a power save mode. In FIG. 14, the horizontal axis represents time, and the vertical axis represents cartridges ID1 to ID6. The ID1 to ID6 are respective identification numbers of the cartridges 20a to 20f. A timeslot is a periodical time span, and the cycle T of a timeslot is predefined. Operation periods X1 to X6 of respective cartridges for each timeslot are determined in accordance with the cycle T of a timeslot and mixing information on perfumes. For example, when the cycle T is 6 seconds and the mixing ratio of the perfumes A to F is 6:3:2:0:1:0, the operation periods X1 to X6 of the cartridges 20a to 20f are determined to be 3 seconds, 1.5 seconds, 1 second, 0 second, 0.5 seconds, and 0 second, respectively. In the present embodiment, the sum of the operation periods X1 to X6 is equal to the cycle T of a timeslot. Note that the length of the cycle T may be any length such as 10 seconds, 30 seconds, 60 seconds, or the like without being limited to the above.

At time 0, that is, the start time of timeslot 01, first, the cartridge ID1 starts atomization. The cartridge ID1 suspends the atomization after the operation period X1 elapses from the start of the atomization. In response to the cartridge ID1 suspending the atomization, the cartridge ID2 then starts atomization and suspends the atomization after the operation period X2 elapses from the start of the atomization. Similarly, the subsequent cartridges ID3 to ID6 sequentially start and suspend atomization. Since the operation periods X4 and X6 of the cartridges ID4 and ID6 are 0 second, the cartridges ID4 and ID6 do not perform atomization as a result. Also at the start of the next timeslot 02, start and suspension of atomization are performed sequentially from the cartridge ID1 (the cartridges ID4 and ID6 do not perform atomization). Similarly, in the subsequent timeslots, the cartridges ID1 to ID6 intermittently repeat atomization operations. Note that the sum of the operation periods X1 to X6 may be shorter than the cycle T of a timeslot. For example, atomization by the cartridges ID1 to ID6 may be sequentially performed from the time of start of a timeslot, and atomization from all the cartridges may be suspended from the time when atomization by the last cartridge ID 6 ends to the time when the current timeslot ends.

In the present embodiment, since one of the cartridges ID1 to ID6 is driven at any time, the peak of power consumption due to simultaneous driving of multiple cartridges can be reduced, and power consumption within each timeslot can be smoothed.

Modified Embodiments

The embodiments described above illustrate mere embodied examples in implementing the present invention, and the technical scope of the present invention is not construed in a limiting sense by the above. That is, the present invention is not limited to the embodiments described above and can be changed within the scope not departing from the spirit of the present invention.

For example, the capacity of a cartridge which contains water may be larger than the capacity of cartridges which contain perfumes, a drive period of an ultrasonic vibrator used for atomizing water may be controlled in accordance with mixing information on perfumes. Further, the timing of starting the operation of each cartridge in a timeslot may be any timing, and the time of starting the operation of respective cartridges in a timeslot can be different for respective cartridges.

Note that a drive source used for atomizing perfumes and water contained in cartridges is not limited to an ultrasonic vibrator. For example, a heating member such as a heater may be provided in a cartridge, and perfumes and water may be volatilized by heating.

REFERENCE SIGNS LIST 10 fragrance generation device
11 casing
12 top cover
13 lid
14 atomization hole
20 cartridge
21 storage plate
22 fan
23 battery
24 water container
30 control circuit board
201 perfume container
202 vibrator case
202a emission hole
203 liquid absorption member
204 connection portion
210 ultrasonic vibrator
300 control unit
301 memory
310 drive circuit

The invention claimed is:

1. A fragrance generation device comprising:
a first ultrasonic vibrator provided in a water container that contains water and used for atomizing the water;
a first emission hole used for emitting the water atomized by the first ultrasonic vibrator;
a plurality of second ultrasonic vibrators provided in a plurality of perfume containers that individually contain multiple types of perfumes, respectively, and used for atomizing the perfumes;
a plurality of second emission holes arranged around the first emission hole and used for emitting the perfumes atomized by the plurality of second ultrasonic vibrators; and
a control unit configured to control driving of the first ultrasonic vibrator and the second ultrasonic vibrators.

2. The fragrance generation device according to claim 1, wherein the control unit controls drive periods of the plurality of second ultrasonic vibrators individually based on mixing information on the multiple types of perfumes.

3. The fragrance generation device according to claim 2 further comprising a wireless communication unit used for receiving the mixing information.

4. The fragrance generation device according to claim 1, wherein the control unit continuously drives the first ultrasonic vibrator.

5. The fragrance generation device according to claim 1, wherein the plurality of second emission holes are arranged in an annular shape in a plan view.

6. The fragrance generation device according to claim 1 further comprising:
the water container in which the first emission hole is formed in an upper part;
the plurality of perfume containers in which the plurality of second emission holes are formed in an upper part, respectively;
a casing that stores the water container and the plurality of perfume containers; and
a fan provided under the water container and the plurality of perfume containers inside the casing and configured to generate an airflow toward an upper part of the casing.

7. The fragrance generation device according to claim 6, wherein the atomized water and the atomized perfumes are mixed in a space inside the casing and emitted outward from an atomization hole formed in an upper part of the casing.

8. The fragrance generation device according to claim 6, wherein each of the perfume containers is a cartridge that is removable with respect to the casing.

9. The fragrance generation device according to claim 1, wherein the water container is a cartridge that is removable from the casing.

10. The fragrance generation device according to claim 1, wherein the water container is fixed to the casing and stores water supplied via the first emission hole.

11. The fragrance generation device according to claim 10, wherein the first ultrasonic vibrator is provided on a bottom of the water container.

12. A fragrance generation device comprising:
a plurality of perfume containers that individually contain multiple types of perfumes, respectively;
a plurality of ultrasonic vibrators provided in the plurality of perfume containers, respectively, and used for atomizing the perfumes;
a water container that is surrounded by the plurality of perfume containers; and
a control unit configured to determine drive periods of the plurality of ultrasonic vibrators in a predetermined cycle individually based on mixing information on the multiple types of perfumes.

13. The fragrance generation device according to claim 12, wherein the mixing information includes types and a mixing ratio of perfumes, and the control unit identifies types of perfumes to be atomized by respective ultrasonic vibrators and determines the drive periods in accordance with the mixing ratio.

14. The fragrance generation device according to claim 13, wherein the control unit determines the drive periods when the mixing information is received from an external device.

15. The fragrance generation device according to claim 12, wherein the control unit drives respective ultrasonic vibrators from time when the cycle starts to time when the drive period elapses.

16. The fragrance generation device according to claim 1, wherein the water container is in a removable cartridge.

17. The fragrance generation device according to claim 1, wherein each of the vibrators includes a plate-shape piezoelectric ceramic and an electrode formed on both faces of the each of the vibrators.

18. The fragrance generation device according to claim 12, wherein each of the vibrators includes a plate-shape piezoelectric ceramic and an electrode formed on both faces of the each of the vibrators.

19. The fragrance generation device according to claim 1, wherein each of the plurality of vibrators is held by a recess formed in a liquid absorption member.

20. The fragrance generation device according to claim 1, wherein the first emission hole is arranged on a surface on which the plurality of second emission holes are arranged.

* * * * *